United States Patent
Cummins et al.

(10) Patent No.: US 10,746,683 B2
(45) Date of Patent: Aug. 18, 2020

(54) CAPACITIVE SENSOR AND METHOD OF USE

(71) Applicant: ALTRATECH LIMITED, Limerick (IE)

(72) Inventors: Timothy Cummins, Cratloe (IE); Brian O'Farrell, Watergrasshill (IE)

(73) Assignee: ALTRATECH LIMITED, County Clare (IE)

( * ) Notice: Subject to any disclaimer, the term of this patent is extended or adjusted under 35 U.S.C. 154(b) by 0 days.

(21) Appl. No.: 15/101,268

(22) PCT Filed: Dec. 10, 2014

(86) PCT No.: PCT/EP2014/077170
§ 371 (c)(1),
(2) Date: Jun. 2, 2016

(87) PCT Pub. No.: WO2015/086654
PCT Pub. Date: Jun. 18, 2015

(65) Prior Publication Data
US 2017/0023512 A1 Jan. 26, 2017

(30) Foreign Application Priority Data
Dec. 12, 2013 (EP) .................................... 13197027

(51) Int. Cl.
*C12Q 1/68* (2018.01)
*G01N 27/22* (2006.01)
(Continued)

(52) U.S. Cl.
CPC ......... *G01N 27/221* (2013.01); *C12Q 1/6825* (2013.01); *G01N 27/223* (2013.01);
(Continued)

(58) Field of Classification Search
CPC ........... G01N 27/3276; G01N 33/5438; G01N 27/22; G01N 27/745; Y10T 29/49117;
(Continued)

(56) References Cited

U.S. PATENT DOCUMENTS 4,822,566 A * 4/1989 Newman ............ G01N 33/5438
324/687
5,413,924 A * 5/1995 Kosak ...................... C12Q 1/68
435/177

(Continued)

FOREIGN PATENT DOCUMENTS

CN 101724695 A 6/2010
CN 103261892 A 8/2013
(Continued)

OTHER PUBLICATIONS

Chang et al "A CMOS magnetic microbeaad-based capacitive biosensor array with on-chip electromagneitc manipulation", Biosnsors and Bioelectronics, Jan. 29, 2013, 45: 6-12. (Year: 2013).*
(Continued)

*Primary Examiner* — Betty J Forman
(74) *Attorney, Agent, or Firm* — Brown Rudnick LLP; Thomas C. Meyers

(57) ABSTRACT

An analyte in a liquid sample is detected using a capacitive sensor having electrodes and a sensor surface, and a signal processor. The sample is dried to reduce its liquid content, and capacitive measurements are made after the drying and preferably also before the drying. The sample may include particles, and the analyte is part of or attached to the particles, and the particles provide a major part of the capacitance change compared to absence of particles. In another example the particles are degenerative and form an integral mass upon application of heat, enhancing the extent of capacitance change.

18 Claims, 12 Drawing Sheets

Negative control sensor equivalent circuit

(51) Int. Cl.
  *G01N 27/327* (2006.01)
  *G01N 33/543* (2006.01)
  *C12Q 1/6825* (2018.01)
  *G01R 27/26* (2006.01)
  *G01N 27/74* (2006.01)

(52) U.S. Cl.
  CPC ....... *G01N 27/3276* (2013.01); *G01N 33/543* (2013.01); *G01N 33/5438* (2013.01); *G01R 27/2605* (2013.01); *G01N 27/745* (2013.01)

(58) Field of Classification Search
  CPC ............... Y10T 436/11; Y10T 436/25; Y10T 436/2575; Y10T 436/144444; C12Q 1/6825; C12Q 2563/116; C12Q 2565/519; G01R 27/2605
  See application file for complete search history.

(56) References Cited

U.S. PATENT DOCUMENTS

| | | | | |
|---|---|---|---|---|
| 6,548,311 | B1* | 4/2003 | Knoll | C12Q 1/6825 205/777.5 |
| 2003/0013185 | A1 | 1/2003 | Saraf | |
| 2004/0005582 | A1* | 1/2004 | Shipwash | G01N 33/54366 435/6.19 |
| 2004/0023253 | A1* | 2/2004 | Kunwar | C12Q 1/003 435/6.11 |
| 2004/0234970 | A1* | 11/2004 | Yoo | B82Y 30/00 435/6.12 |
| 2004/0235028 | A1* | 11/2004 | Franzen | C12Q 1/6816 435/6.11 |
| 2005/0069905 | A1* | 3/2005 | Myerholtz | G01N 33/5438 435/6.19 |
| 2005/0218465 | A1 | 10/2005 | Cummins | |
| 2006/0105373 | A1* | 5/2006 | Pourmand | B82Y 15/00 435/6.11 |
| 2009/0008248 | A1 | 1/2009 | Shimomura et al. | |
| 2010/0089769 | A1 | 4/2010 | Ulmer et al. | |
| 2010/0227416 | A1* | 9/2010 | Koh | C12Q 1/6837 436/501 |
| 2013/0189687 | A1 | 7/2013 | Tanaka | |

FOREIGN PATENT DOCUMENTS

| | | |
|---|---|---|
| EP | 2 233 920 A1 | 9/2010 |
| JP | 2004-061144 A | 2/2004 |
| WO | 88/10272 A1 | 12/1988 |
| WO | 99/14596 A1 | 3/1999 |
| WO | 2012/028719 A2 | 3/2012 |

OTHER PUBLICATIONS

Dynal "Biomagnetic Techniques in Molecular Biology", 1998, Heidelberg, Germany, pp. 7, 10. (Year: 1998).*
International Preliminary Report on Patentability and Written Opinion of the International Searching Authority; PCT/EP2014/077170 dated Jun. 14, 2016.
International Search Report issued in PCT/EP2014/077170; dated Mar. 19, 2015.
Claudio Stagni et al.; "CMOS DNA Sensor Array With Integrated A/D Conversion Based on Label-Free Capacitance Measurement"; IEEE Journal of Solid-State Circuits; Dec. 2006; pp. 2956-2964; vol. 41; No. 12; IEEE.
Claudio Stagni et al.; "A Fully Electronic Label-Free DNA Sensor Chip"; IEEE Sensors Journal; Apr. 2007; pp. 577-585; vol. 7; No. 4; IEEE.
Claudio Stagni Degli Eposti et al.; "Fully Electronic CMOS DNA Detection Array Based on Capacitance Measurement with On-Chip Analog-to-Digital Conversion"; Digest of Technical Papers; 2006 IEEE International Solid-State Circuits Conference; Feb. 6, 2006; pp. 1-10; IEEE.
L. Moreno-Hagelsieb et al.; "Sensitive DNA electrical detection based on interdigitated Al/Al2O3 microelectrodes"; Sensors and Actuators B; 2004; pp. 269-274; 98; Elsevier.
G. Stoner et al.; "Adsorption of Blood Proteins on Metals Using Capacitance Techniques"; The Journal of Physical chemistry; p. 1088.

* cited by examiner

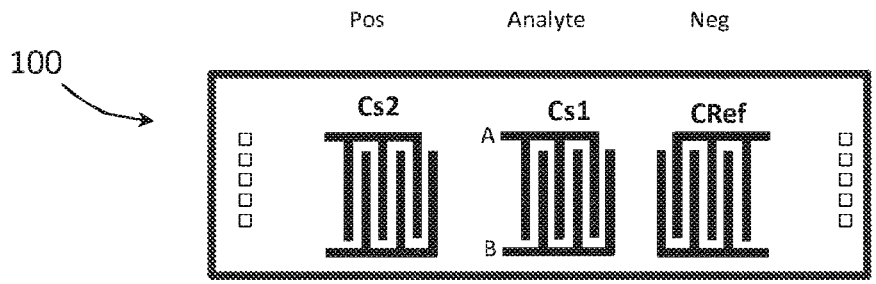
Fig 7(a)
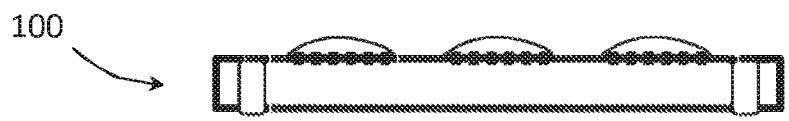
Fig 7(b)
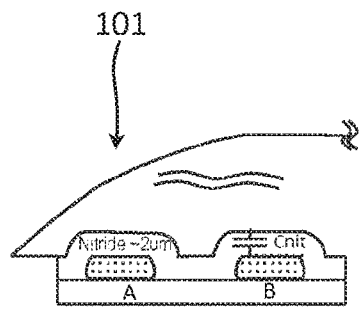
Fig 8 (a): Negative control sensor
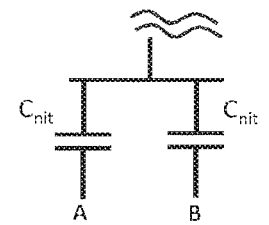
Fig 8 (b) equivalent circuit
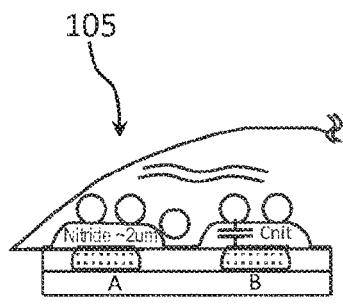
Fig 8 (c): Analyte Sensor
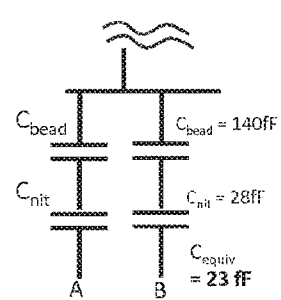
Fig 8 (d): equivalent circuit

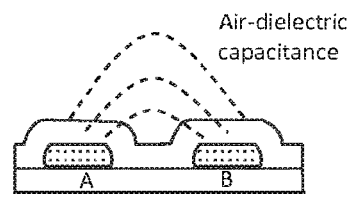
Fig 9 (a): Negative control sensor
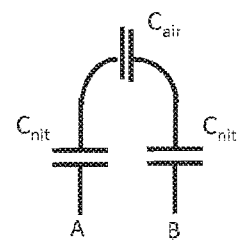
Fig 9 (b): equivalent circuit
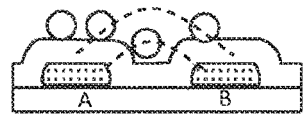
Fig 9 (c): Analyte Sensor
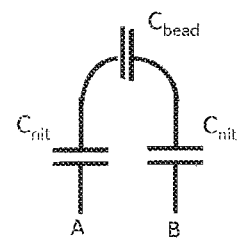
Fig 9 (d) equiv circuit
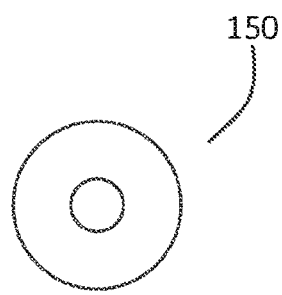
Fig 10(a)
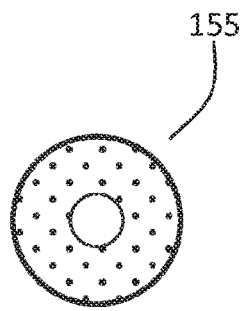
Fig 10(b)

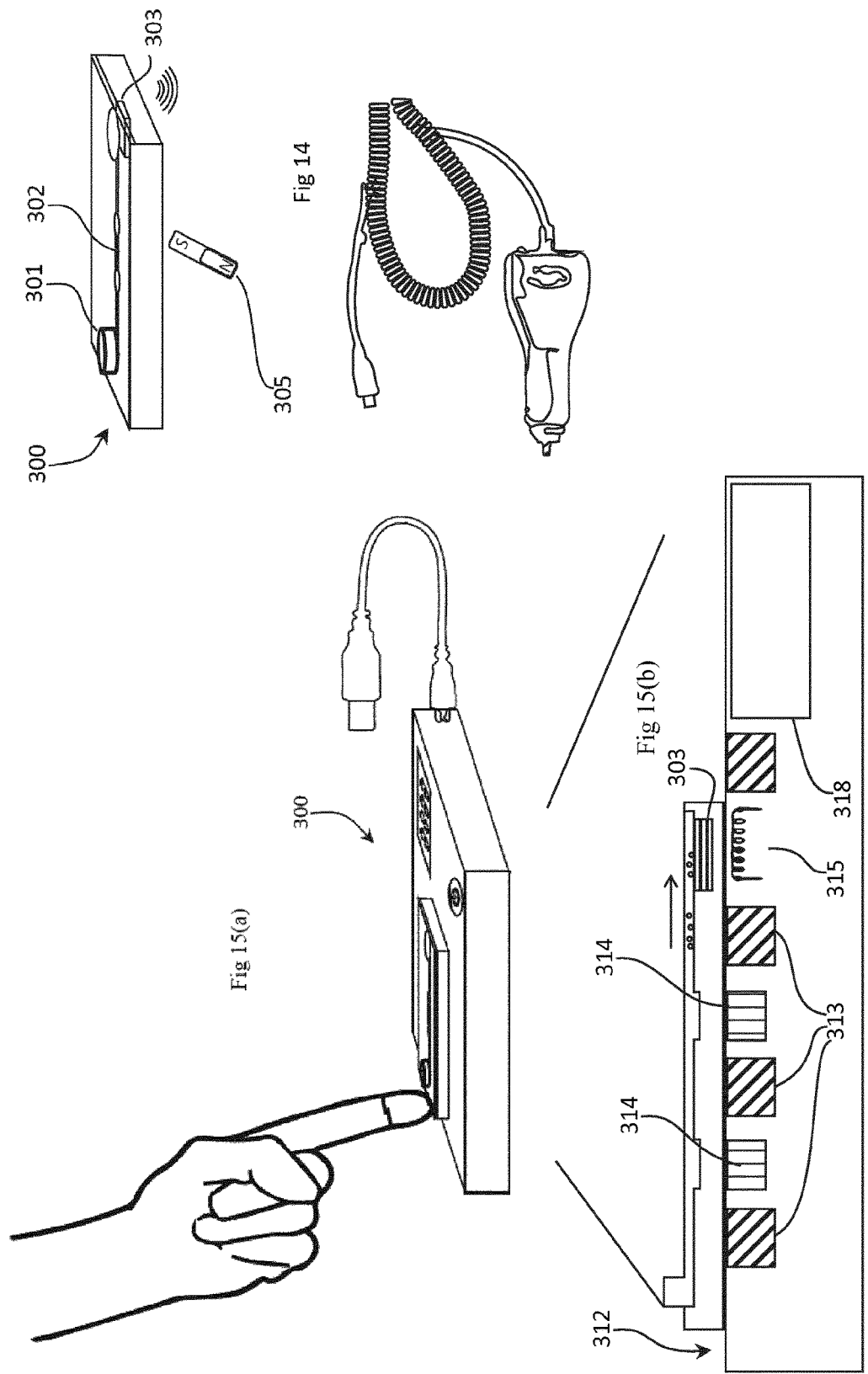

CAPACITIVE SENSOR AND METHOD OF USE

The invention relates to capacitive sensors arranged to detect and quantify an analyte in a liquid sample over a sensor surface.

Such capacitive sensors are known, being described for example in "Adsorption of Blood Proteins on Metals Using Capacitance Techniques", by Stoner et al, The Journal of Physical Chemistry, Vol. 74, No. 5, Mar. 5, 1970. This describes two working electrodes upon which blood proteins adsorb, thereby changing the capacitance between the electrodes. A third (reference) electrode is shown immersed in the liquid, to control the DC voltage. While this arrangement appears effective for the target blood proteins, it is notable that the working electrodes are large (0.05 cm$^2$) to obtain sufficient capacitance (microfarads) to be measured externally, and are made of noble metals (gold, platinum, mercury) to reduce corrosion, oxidation, or reaction with the liquid solution. The reference electrode is formed of platinized platinum. The resulting apparatus therefore appears to be large, made of expensive noble and precious metals, and apparently not amenable to miniaturisation, portability, and high-volume low cost manufacturing. It also appears that it is not amenable to measuring smaller (femtoFarad or atto-Farad) capacitance of nanometre components such as beads, nano-particles, or DNA and RNA molecules. Such sensitivity is required for direct quantification of, for instance, biological analytes such as DNA. Since that paper, many publications in the interim, e.g. U.S. Pat. No. 8,105,478, have proposed variations such as gold-electrodes, silver-chloride reference electrodes, and integration on silicon substrates containing charge amplifier circuits. But, these materials are expensive and not readily available on high-volume low-cost standard CMOS semiconductor technologies. And particles of the reference electrode material may even interfere with the analyte being measured.

The paper by Morena-Hagelsieb et al: "Sensitive DNA electrical detection based on interdigitated Al/Al2O3 microelectrodes", Sensors and Actuators B:Chemical, vol. 98, no. 2-3, 15 March 2004, pp. 269-274 describes various electrical-based methods for detection of DNA.

US2013/0189687 (Panasonic Corp.) describes a method for measuring pyrophosphoric acid and SNP typing. This is an electrochemical sensor, measuring current at the nano-Amps level.

JP2004061144 (Japan Science and Tech Corp) describes an antigen-antibody reaction detection method, using a magnetic field sensor.

WO88/10272 (Nicholson) describes a method of preserving a body fluid sample. This involves drying a blood sample for ease of transport and then re-hydrating the sample for testing.

An object of this invention is to provide a sensor which is more compact and portable, and/or more robust, and/or less expensive to manufacture, and/or which has greater sensitivity to presence of nanometre-scale target components. Another objective is to avoid reference electrodes and expensive noble metals. Another objective is to eliminate corrosion and drift problems of electrodes; and to ensure that the sensor does not degrade or interfere with the analyte material.

SUMMARY OF THE INVENTION

According to the invention, there is provided a method of detecting an analyte in a liquid sample using a capacitive sensor having electrodes and a sensor surface, and a processor linked with the electrodes, the method comprising the steps of:
bringing the sample into contact with said sensor surface,
measuring capacitance of the sample, and
using said measurement to provide data concerning the analyte.

In one embodiment, the method comprises the steps of drying the sample and measuring capacitance of the dried sample.

In one embodiment, the method comprises the further steps of:
measuring capacitance of the sample before drying, and
deriving analyte data from both said measurements made before and after drying.

In one embodiment, the sample includes particles, and the analyte is part of or attached to said particles, and said particles provide a major part of a capacitance change.

In one embodiment, the particles are beads which are attached to analyte molecules. Preferably, the analyte molecules are target nucleic acid (NA) molecular strands such as DNA or RNA.

In one embodiment, the sensor has a CMOS architecture in which CMOS layers provide the electrodes and signal processing circuitry (10). Preferably, the electrodes (3, 4) are covered by a protection layer (5). In one embodiment, the electrodes are covered by nitride.

In one embodiment, the sensor has a planar top surface without features such as bond wires. In one embodiment, the sensor includes a TSV chip. In one embodiment, the protection layer thickness is in the range of 1 μm to 3 μm.

In one embodiment, the sensor comprises a sensing capacitor ($C_s$) and a reference metal-insulator-metal (MIM) capacitor ($C_r$) and said capacitors form the front-end (11) of a second-order sigma-delta switched-capacitor modulator A-to-D converter (12) providing a one-bit digital output bit stream representing the charge balancing between sensing and reference capacitors, and a filter (13) for averaging the bit-stream to provide a digital output word.

In one embodiment, the sample is dried by a heater incorporated within the layers of a CMOS structure which includes the electrodes at a top level. In one embodiment, the signal processor monitors the rate of evaporation of sample liquid to provide a characteristic signature for the analyte. In one embodiment, the sample is milk, and the method determines protein and/or casein concentration.

In one embodiment, the sensor includes a probe fixed on the sensor surface, said probe being selected to attach to a target NA analyte in the sample, and the measurements are made after said attachment. Preferably, the sensor has a nickel-coating to selectively bind his-tagged proteins. In one embodiment, the surface has a thiol self-assembled-monolayer (SAM) to bind DNA or PNA probes.

In one embodiment, the method comprises the step of providing a PNA probe for binding to the analyte.

In one embodiment, the method comprises the steps of:
providing PNA probes n the sensor surface and attracting DNA molecules to the sensor surface by temporarily stopping the signal processor and placing a positive voltage on a plurality of the electrodes of the sensor and,
once the target DNA molecules are bound to the PNA probes, a negative voltage is then applied to said electrodes to repel any non-specifically bound DNA molecules, whereas the specifically-bound target DNA molecules stay tethered at the surface due to the Watson-Crick complementary binding energies, and resume operation of the signal processor to measure capacitance.

In one embodiment, the signal processor modulates electrode drive frequency and enable spectral analysis of the analyte at the surface, to assist distinguishing between big and small particles, or between bound and un-bound molecules. Preferably, the modulation is performed to monitor the effects of changing electric field applied across the analyte. In one embodiment, the monitoring is performed to monitor ability of the charges to separate, and how fast this redistribution happens, which depends on the size of the molecules and how strongly they are bound, and in which charges that are loosely bound respond to the electric field at higher frequencies, and vice versa.

In one embodiment, the beads are chosen to have a K value of approximately 10 to 14. In one embodiment, the beads are a composite of ferrite and polystyrene.

In one embodiment, the electrodes are arranged to provide analyte, negative and reference sensors, and are calibrated with a positive fluid or buffer solution containing a known amount of beads to be measured; an analyte channel containing the same fluid or buffer solution, with an unknown amount of beads to be determined; and a negative channel containing the same fluid or buffer solution with none of the target beads present. Preferably, the beads comprise paramagnetic material encased in a wax material.

In one embodiment, the method comprises the step of at least partially melting the beads on the sensor surface until they form a wax layer, and measuring capacitance after said melting. In one embodiment, the beads are melted by operation of a heater within a multi-layer CMOS sensor structure.

In one embodiment, the method comprises the step of applying a magnetic field to attract the beads to the sensor surface.

In one embodiment, the method comprises the step of attracting target Nucleic Acid molecules to the sensor surface so that they act as a ligand tethering a magnetic bead to the surface due to Watson-Crick pairing of the NA to a first complementary probe on the bead, and to a second complementary probe immobilised on the sensor surface, and then applying a magnetic field at a level so that the beads stay bound initially due to the NA-PNA Watson-Crick binding energies, applying heat to the sample until the temperature reaches the characteristic NA-probe melting temperature at which some bonds break and some beads are pulled away under magnetic attraction, and monitoring real time capacitance change.

In one embodiment, the target NA and the probe have a single base pair difference.

In one embodiment, the sensor surface has a plurality of different sensor regions, each with a different immobilized probe, and differential sensing is performed.

In one embodiment, the sample is such that beads are tethered to a first probe region by a wild type sequence, and by a mutant type sequence above a second sensor region, there is a negative control sensor region where no beads attach, and a magnet pulls away beads which are released when the melting temperature is reached.

In another aspect, the invention provides a sensing apparatus comprising a sensor comprising capacitive electrodes beneath a sensor surface, and a processor linked with the electrodes, wherein the apparatus comprises means for:
bringing the sample into contact with said sensor surface, measuring capacitance of the sample, and
using said measurement to derive data concerning the analyte.

In one embodiment, the sensor has a CMOS architecture in which CMOS layers provide the electrodes and signal processing circuitry. In one embodiment, the electrodes (are covered by a protection layer, preferably having a thickness in the range of 1 µm to 3 µm.

In one embodiment, the electrodes are covered by nitride.

In one embodiment, the sensor has a planar top surface without features such as bond wires. In one embodiment, the sensor includes a TSV IC, the planar top surface of which is the sensor surface. In one embodiment, the sensor incorporates a surface heater within a CMOS layer.

In one embodiment, the sensor comprises a sensing capacitor ($C_s$) and a reference metal-insulator-metal (MIM) capacitor ($C_r$) and said capacitors form the front-end of a second-order sigma-delta switched-capacitor modulator A-to-D converter providing a one-bit digital output bit stream representing the charge balancing between sensing and reference capacitors, and a filter for averaging the bit-stream to provide a digital output word.

In one embodiment, the sensor includes a probe fixed on the sensor surface, said probe being selected to attach to a target NA analyte in the sample, and the measurements are made after said attachment. In one embodiment, the sensor has a nickel-coating to selectively bind his-tagged proteins. In one embodiment, the surface has a thiol self-assembled-monolayer (SAM) to bind DNA or PNA probes.

In one embodiment, the electrodes are arranged to provide analyte, negative and reference sensors, and are calibrated with a positive fluid or buffer solution containing a known amount of beads to be measured; an analyte channel containing the same fluid or buffer solution, with an unknown amount of beads to be determined; and a negative channel containing the same fluid or buffer solution with none of the target beads present.

In one embodiment, the sensor surface has a plurality of different sensor regions, each with a different immobilized probe, and differential sensing is performed. In one embodiment, the sensor is mounted in a catheter suitable for insertion in a blood vessel. In one embodiment, the apparatus comprises a sealed disposable cartridge housing the sensor and further comprises a wireless transceiver.

In one embodiment, the apparatus comprises a magnet to control flow of the magnetic beads in a sample. In one embodiment, the apparatus comprises a bench-top apparatus for receiving the cartridge.

In one embodiment, the sensor comprises only two sensing electrodes, without a reference electrode.

DETAILED DESCRIPTION OF THE INVENTION

The invention will be more clearly understood from the following description of some embodiments thereof, given by way of example only with reference to the accompanying drawings in which:

FIG. 1(a) shows a CMOS semiconductor integrated circuit (IC) sensor of the invention providing inter-digitated capacitive electrodes; FIG. 1(b) shows a cross-section diagram of the CMOS IC; FIG. 1(c) shows a cross-section of two electrodes (A and B) of one of the capacitive sensors; and FIG. 1(d) is an electrical schematic of the sensing capacitor and a reference capacitor forming the differential front-end of a sigma-delta converter;

FIG. 1(e) shows a cross-section of a TSV version of the CMOS IC, with an analyte droplet dispensed on the sensor;

FIG. 1(f) shows a top-view photo of a circular sensor; FIG. 1(g) shows a 0.4 µl droplet on the sensor; FIG. 1(h)

shows the sensor with particles on the sensor after droplet evaporation; and FIG. 1(j) shows a close-up SEM image (approx. 10,000×) of some particles on the sensor between electrodes; and FIG. 1(k) is a SEM image with magnification 5,000× showing about 200 beads of average diameter about 2 µm on a sensor surface;

FIG. 1(l) is a cross-sectional diagram through a sensor, showing a raised area encircling a sensor surface, for example a hydrophobic polyimide layer;

FIGS. 2(a) and (b) illustrate "wet" operation of the sensor, in which the FIG. 2(b) plot shows capacitance vs. salinity;

FIGS. 2(c) and 2(d) illustrate "dry" operation of the sensors after the saline solution has been dried or evaporated, in which the FIG. 2(d) plot shows capacitance vs. dry salt quantity;

Figure 10C:
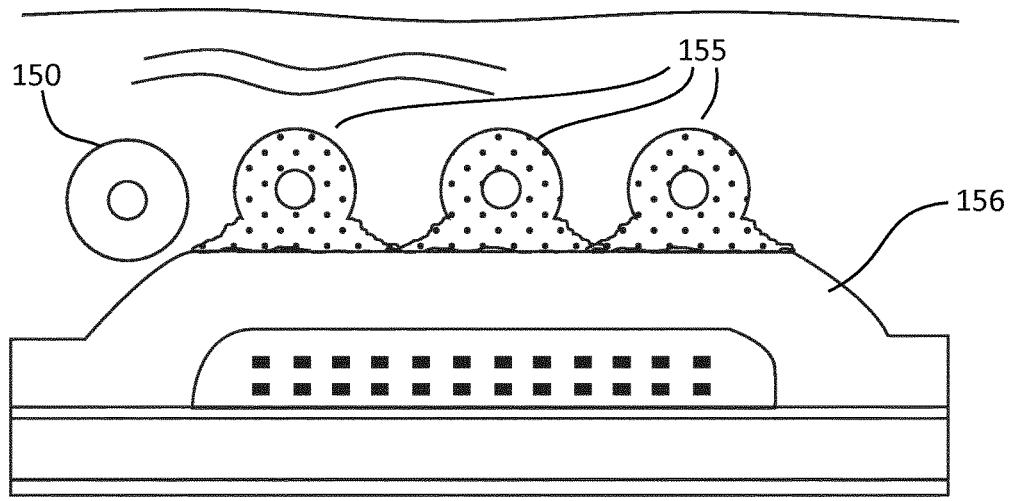
Figure 11:
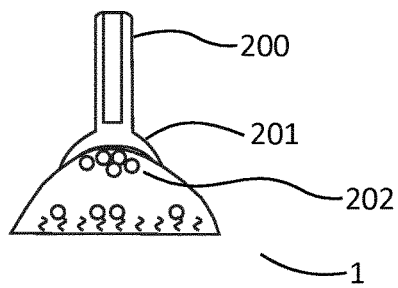
Figure 12A:
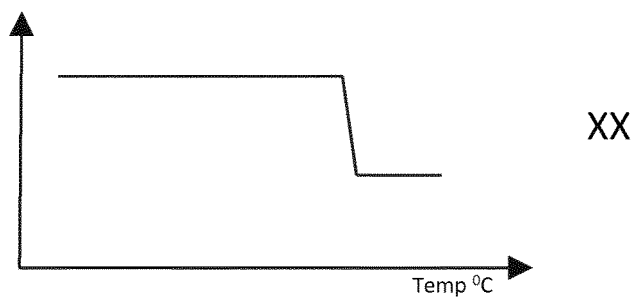
Figure 12B:
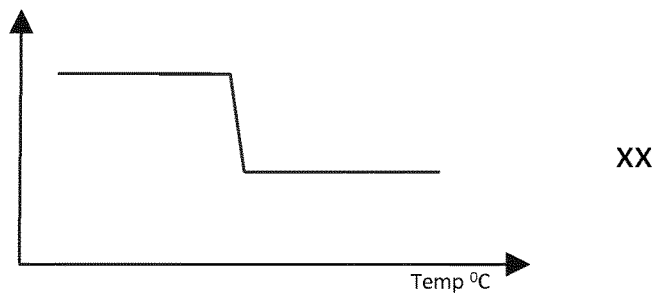
Figure 12C:
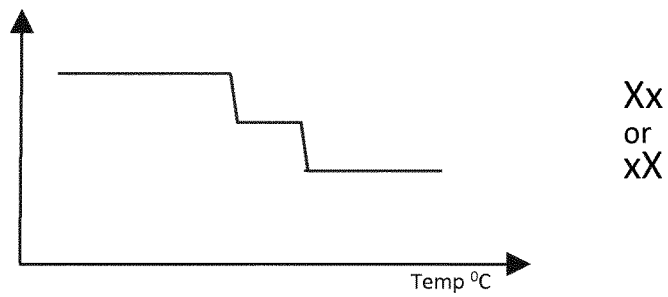
Figures 13A, 13B, 13C:
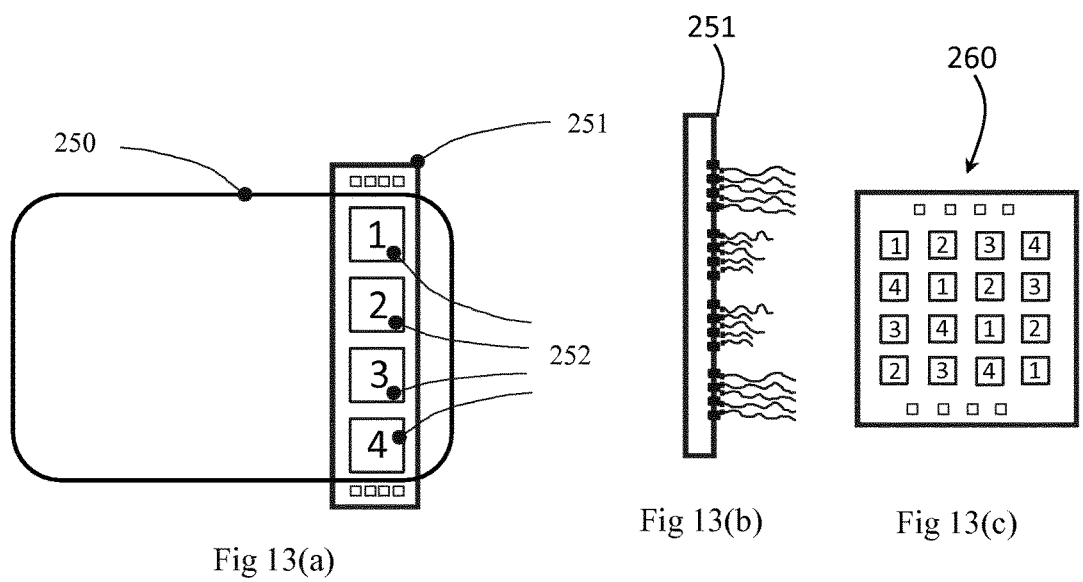
Figure 16:
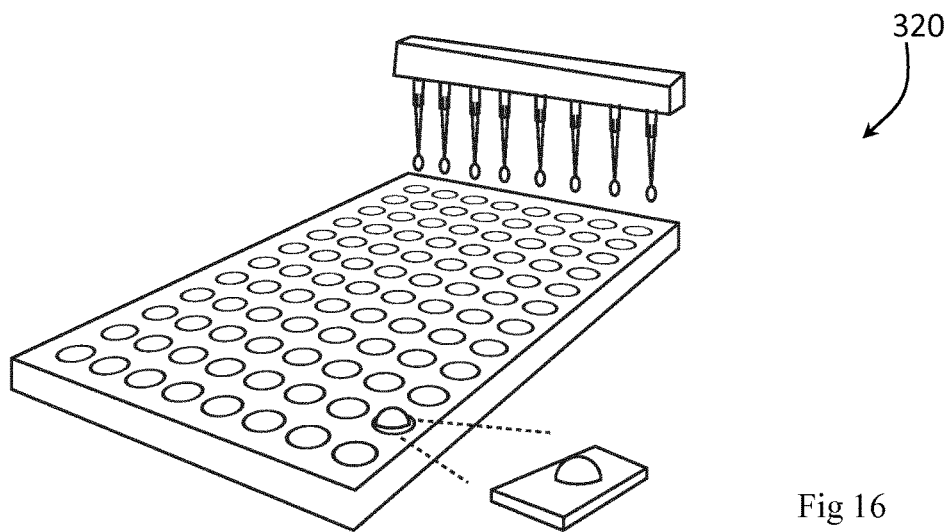
Figure 17:
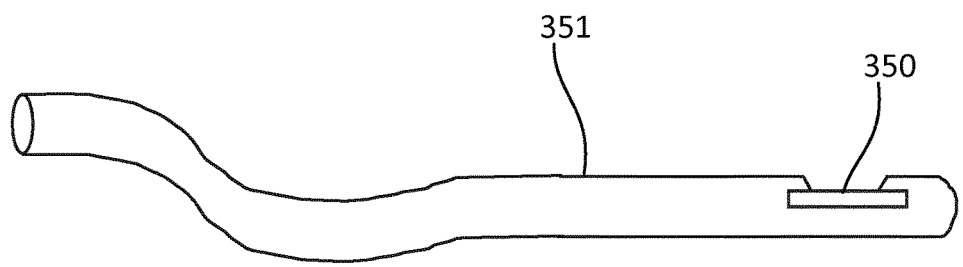
Figure 18:
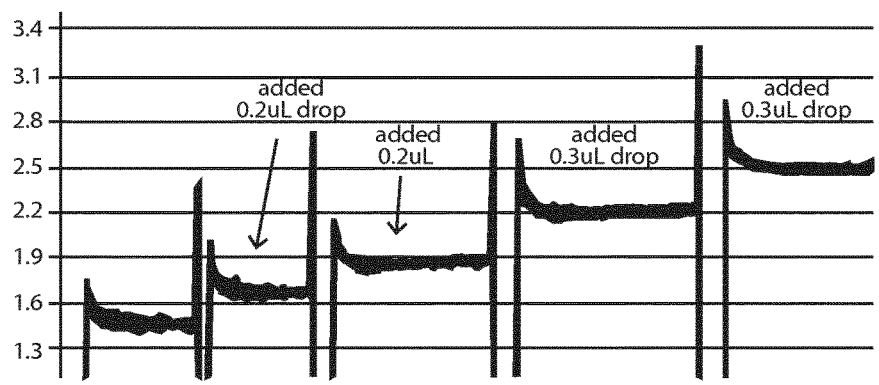
Figure 19:
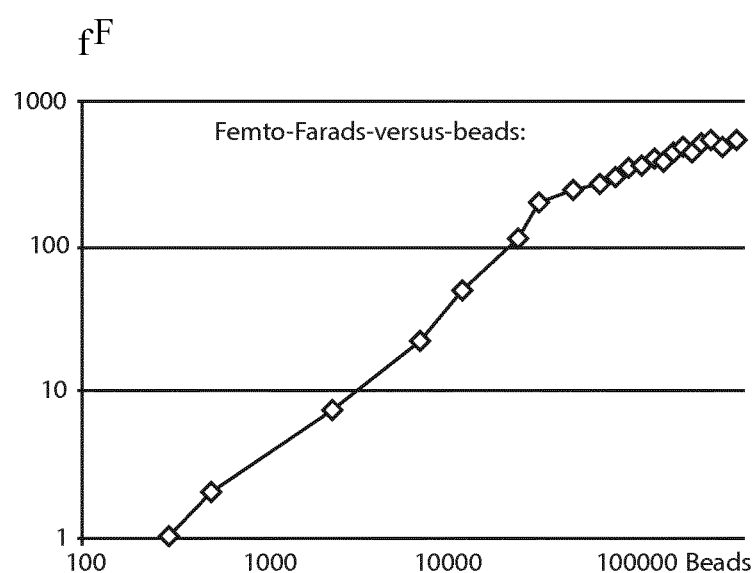

FIGS. 7(a) and 7(b) are diagrammatic plan and side views show a CMOS semiconductor IC containing sensing and reference capacitive sensors of the invention;

FIGS. 8(a) to (d) are diagrams showing wet capacitive measurement of an analyte versus a negative control;

FIGS. 9(a) to (d) show dry capacitive measurement of an analyte versus a negative control;

FIG. 10(a) shows a paramagnetic bead, FIG. 10(b) shows a degenerative paramagnetic bead, and FIG. 10(c) shows diagrammatically degradation of the latter beads on the sensor surface with application of heat;

FIG. 11 shows magnetic force being applied to beads tethered to a sensor surface;

FIGS. 12(a) to (c) are a series of plots showing diagrammatically capacitance changes versus temperature for melting curve analysis;

FIGS. 13(a) and (b) are plan and side view diagrams showing a sensor with four sensor regions, and FIG. 13(c) is a plan view of a variation with sixteen sensor regions;

FIG. 14 is a perspective view of a microfluidic cartridge sensor;

FIG. 15 is a perspective view showing a sensor having a hand-held part and a bench-top reader onto which it fits;

FIG. 16 is a perspective view of a sensor system with an array of sensor ICs;

FIG. 17 shows a sensor in a catheter;

FIG. 18 is a plot showing detected capacitance increase with time for added liquid sample drops; and FIG. 19 is a plot showing detected capacitance increase versus increasing number of beads.

DESCRIPTION OF THE EMBODIMENTS

Figure 1A:
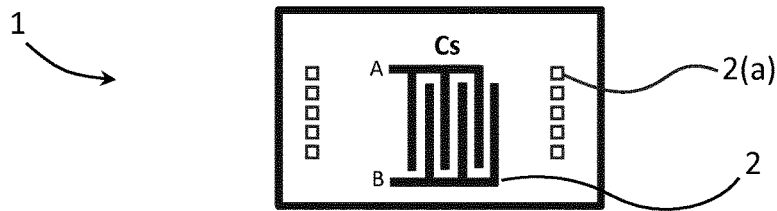

Referring to FIG. 1(a), this shows a plan view of a CMOS sensor 1 of the invention containing a sensing capacitor Cs formed of inter-digitated electrodes 2, and bond pads 2(a) for external signal connection. The diagram is not to scale, for simplicity of illustration. Actual electrode dimensions in this embodiment are 10 µm width, 5 µm spacing, and 15,000 µm total finger length.

Figure 1B:
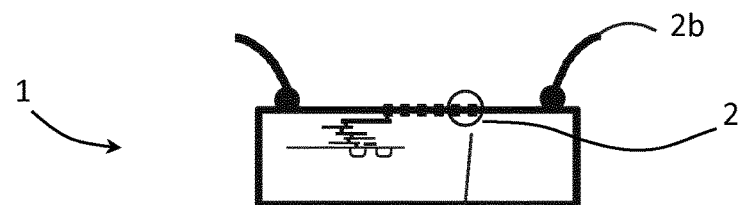

FIG. 1(b) shows a cross-section of the IC 1, again not to scale for simplicity. It has 6 layers of metal interconnect, with the electrodes being formed in the top layer ("Metal-6"). Bond-wires 2(b) are shown attached to the bond pads. One CMOS transistor is shown, representing circuitry integrated on the chip. This includes temperature sensors, heater structures such as metal spirals or substrate diodes, analogue-to-digital converters, substrate and metal-interconnect-metal (MIM) capacitors, a signal processor including logic for controlling the A-to-D switched-capacitor circuits, non-volatile-memory for storing sensor calibration coefficients, and a microcontroller for sensor linearization, compensation, and signal processing; and optionally a radio-frequency transceiver. Fabrication methods of this standard CMOS semiconductor process are known, for example as described in U.S. Pat. No. 5,514,616, which shows all the key steps including transistor source/drain formation, gate deposition, tungsten contacts, CVD oxide deposition, polishing, aluminium metal deposition, and oxy-nitride passivation.

Figure 1C:
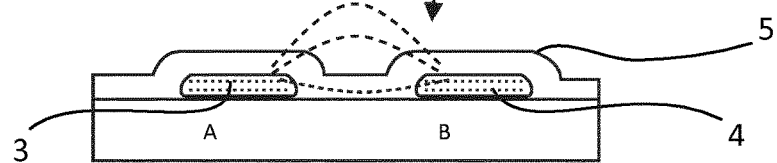

FIG. 1(c) is a close-up view of a pair of the inter-digitated electrodes 3 and 4 (A and B), over which there is a protective layer 5 of nitride. As illustrated by the dashed electric field lines, the capacitance between the electrodes consists of fixed portions in the substrate and nitride, and a variable portion in the air or analyte above the nitride. This variable portion is employed as a sensor signal transducer. In this embodiment the electrodes 3 and 4 are formed of 2 µm thick aluminium. The aluminium fingers are protected beneath the 2 µm nitride layer 5. This eliminates effects such as electrode corrosion, oxidation, and sensor drift. It also presents an inert surface which does not pollute or foul the analytes or particles to be measured.

Figure 1D:
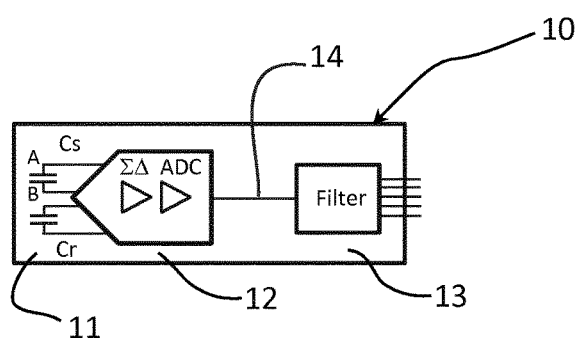

Referring to FIG. 1(d), the sensing capacitor $C_s$, and a reference metal-insulator-metal (MIM) capacitor $C_r$ form the front-end 11 of a second-order sigma-delta switched-capacitor modulator A-to-D converter 12 (as is known in the art, e.g. Malcovati, FIG. 2, VLSI Symposium Digest 1995). The modulator produces a one-bit digital output bit-stream 14 representing the charge balancing between sensing and reference capacitors. The bit-stream is filtered by a filter component 13 and averaged to produce a digital output result with 20 to 24 bits of resolution. The proximity of the electrodes to the analyte (µm) results in little or no parasitic interfering capacitances. The resulting high-resolution analog-to-digital converter is capable of detecting femtoFarad and attoFarad changes in the variable component of the sensing capacitance, due to the differing dielectric constants of various analyte particles. The circuit is self-contained between nodes A and B, eliminating the need for a reference electrode immersed in the analyte solution as is required in prior art capacitive sensors, such as Stoner (1970) referenced earlier. The modulator switched-capacitor frequency in this embodiment is 32 KHz, but this can vary over a wide range of frequencies as is known in the art.

Figure 1E:
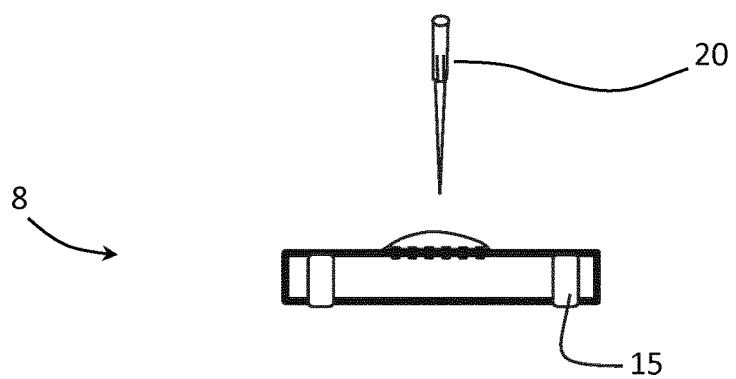

FIG. 1(e) shows a cross-section of an alternative embodiment of the CMOS IC (8), where the I/O connections of the IC are brought from the front to the rear of the IC by Through-Silicon-Vias (TSV) 15. TSV is a recent innovation in the semiconductor industry to reduce overall height of ICs. Via openings are etched from the back of the die (while it is still in wafer form) all the way to the metal interconnect layers at the front of the die. The backside of the wafer is then electroplated with copper to fill the vias, thereby bringing the A-to-D converter signals in the metal interconnect layer from the front (top) of the IC to the rear (back) of the IC. This has the advantage of eliminating bond-wires and topography variations on the top of the IC. This provides a smooth surface with no perturbations, facilitating the flow of fluid analytes across the capacitive sensor surface of the IC, or the dispensing of droplets as shown in the diagram. A typical TSV fabrication process is described in more detail in U.S. Pat. No. 8,513,061.

Figure 1F:
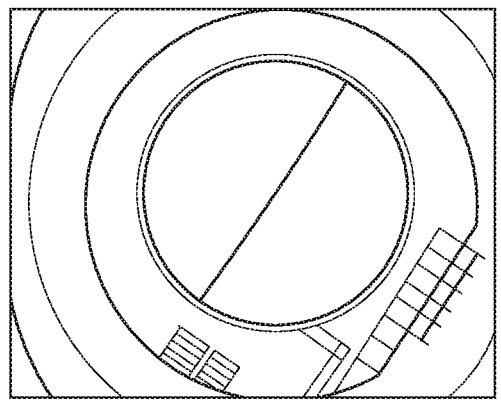
Figure 1G:
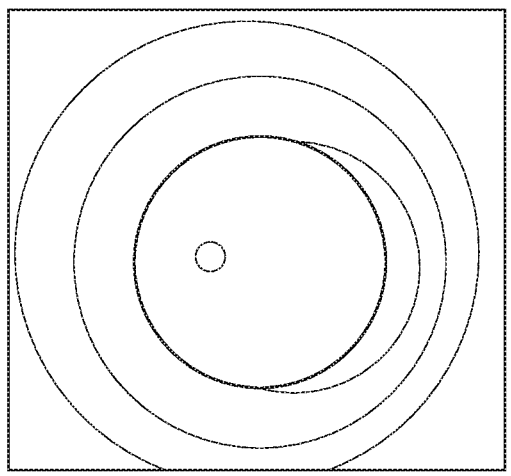
Figure 1H:
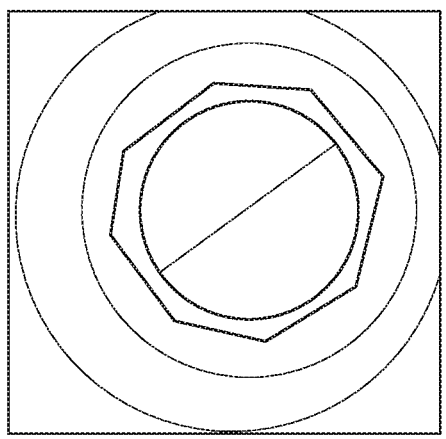
Figure 1J:
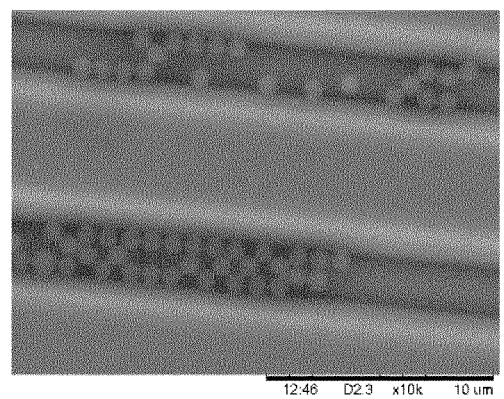
Figure 1K:
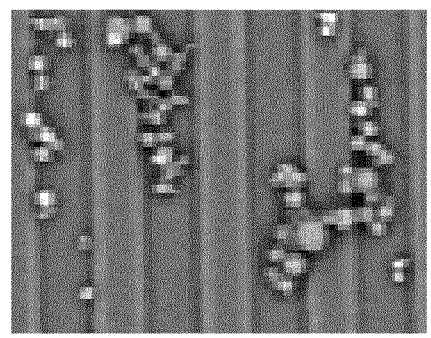

FIGS. 1(f) to 1(h) are actual images (at 100× magnification) of a circular sensor embodiment in operation. FIG. 1(f) shows the sensor at start of assay. FIG. 1(g) shows a droplet with beads on the sensor surface, and FIG. 1(h) shows the sensor surface after drying, with beads being visible on the sensor. FIGS. 1(j) and 1(k) also show dried beads on a sensor as described in more detail below.

Figure 1L:
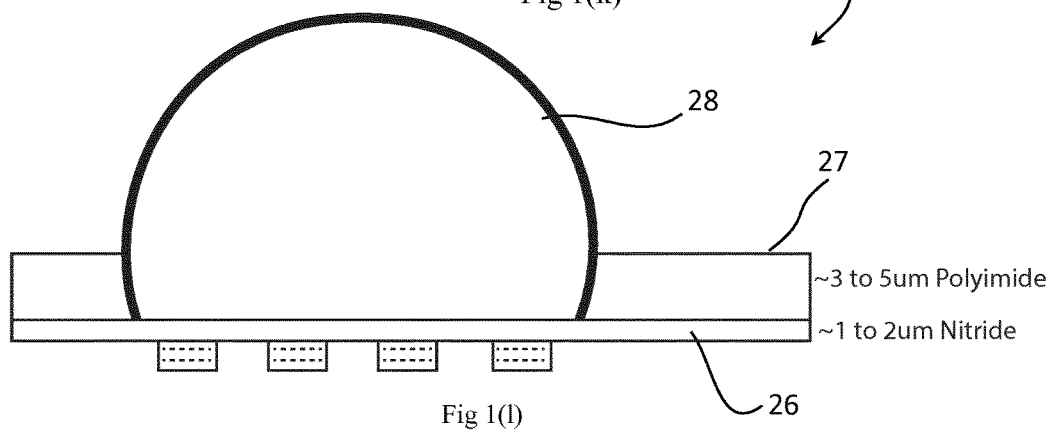

FIG. 1(l) is a cross-sectional diagram through a sensor 25, showing a raised area 27 encircling a sensor surface, for example a hydrophobic polyimide layer. The layer 27 acts as a target to direct and retain the droplet on the sensor, facilitating manual or automated droplet pipetting application. The hydrophobic polyimide later 27 is of 3 to 5 µm thickness, and it is on a substrate 26 of 1 to 2 µm of nitride. Advantageously, the sensor comprises only two sensing electrodes, without a reference electrode.

FIG. 2 shows the invention performing a salinity "wet" measurement, according to the following assay steps:

Create a saturated salt water solution, i.e. 26% by weight or 260 g/L

Dilute this in vials, to 20%, 15%, 10%, 5%, 2.6%, 1.3% solutions.

Figure 2A:
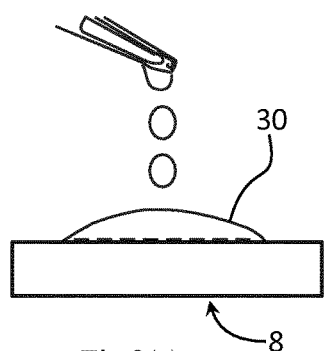

Apply a 0.4 µl droplet 30 of the 1.3% solution on the capacitive sensor on the CMOS IC 8 as shown in FIG. 2(a) or the image of FIG. 1(g). This is a 20:1 dilution, so the droplet contains approx. 6 µg of salt. Log the capacitance reading.

Just before the droplet evaporates, flush with about 10 µl of 2.6% solution, leaving one droplet of this new concentration on sensor; log the capacitance reading.

Repeat for each of the other increasing concentrations.

Figure 2B:
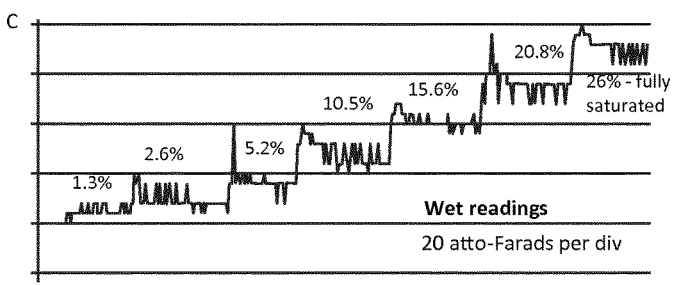

FIG. 2(b) shows the resulting "wet" capacitance readings, at 20 attofarads/div over a horizontal axis of 30 mins (six sequential droplets applied at 5 minute intervals). The capacitance changes in correspondence to salt concentrations increasing from 1.3% to fully saturated 26%. This change is due to the dielectric constant (K) of the solution in the vicinity of the electrodes being changed by salt molecules (K~6) dissolving into solution and displacing water molecules (K~80). Note that the nitride layer protects the electrodes from drift and corrosion by the salt solution.

Wash and rinse the CMOS IC 8 surface to remove all salt.

Figure 2C:
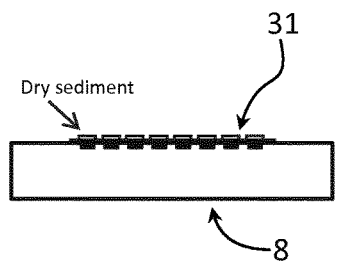
Figure 2D:
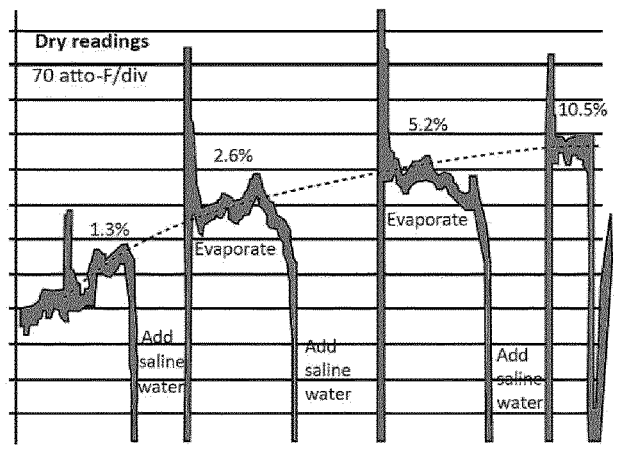

FIGS. 2(c) and 2(d) show a further feature of the invention, "wet" and "dry" capacitance readings for different salt concentrations as per the following assay:

Repeat the above "wet" assay, starting with a droplet of 1.3% solution, but this time allow the droplet to evaporate to provide dry sediment 31. At room temperature the 0.4 µl droplet takes 3 or 4 minutes approx. to evaporate. A 'sediment' layer of salt particles 31 now remains, as shown in FIG. 2(c). The "dry" capacitance reading is then logged.

Add the next droplet, allow to evaporate, then repeat with droplets of increasing concentrations.

FIG. 2(d) shows the "dry" capacitance readings, at 70 attoFarads/div, over a 35 minute period. Three droplets are added, i.e. three 'wet-dry' cycles over the 35 minutes. Each doubling of salt concentration increases capacitance—but by diminishing amounts as the salt sediment layer gets thicker. e.g. 100 aF for $1^{st}$ 6 µg layer, 60 aF for $4^{th}$ layer. The capacitance increases are due to K(salt)=6, versus K(air)=1. The dry layer thicknesses are each less than 100 nano-meters thick. All are detectable, and these 'dry' readings give a 'cross-check' on the wet-readings, for extra accuracy.

Since the capacitance sensor is measuring continuously in real time, it can monitor the rate of evaporation of the droplet, and subsequent time for the sediment layer to fully dry out. This gives valuable 'fingerprint' information on the analyte material and characteristics, for example evaporation and drying-out take much longer for sucrose particles than for salt particles.

Figure 3:
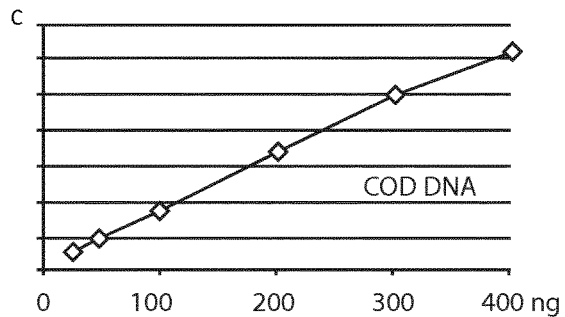
FIG. 3 is a results graph of capacitance vs mass, of the capacitive sensor performing DNA quantification.

FIG. 3 shows the capacitive sensor performing DNA quantification in similar fashion. In this example, Atlantic Cod DNA of 1 microgram per microlitre (1000 ng/µl) is prepared, then a 0.4 µl droplet of this is applied to the sensor (i.e. 400 ng), and allowed to evaporate. Capacitance is measured 'wet' and 'dry', i.e. before and after evaporation. The sensor is rinsed, and the measurements are repeated for 300 ng, 200 ng, 100 ng, 50 ng, and 25 ng. Results are shown in FIG. 3, in which the vertical axes are 100 atto-Farads per division.

It will be appreciated that this "wet and dry" method and apparatus, employing a low-cost CMOS semiconductor sensor, can be used 'on-site' for quantifying a variety of fluids and particles, such as water quality monitoring, or total milk solids.

Figure 4:
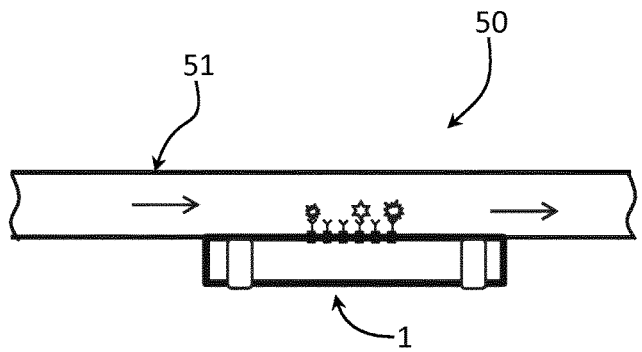
FIG. 4 shows the TSV CMOS IC mounted in a flow channel.

FIG. 4 shows a sensor 50 with the TSV CMOS IC 8 mounted in a flow channel 51. The smooth surface of the TSV IC 8 greatly simplifies and facilitates fluid flow across the sensor, milk flow in this example. Modern dairy production has a particular interest in knowing the protein and casein content in whole milk, for milk quality and animal health reasons. The sensor surface is functionalised with an adsorbed mucosal protein-binding layer. This selectively binds milk proteins in the milk flow. The channel is then flushed with air, and the 'dry' measured capacitance is compared to the initial 'dry' capacitance before binding. The difference is a direct measure of milk protein content.

Figure 5:
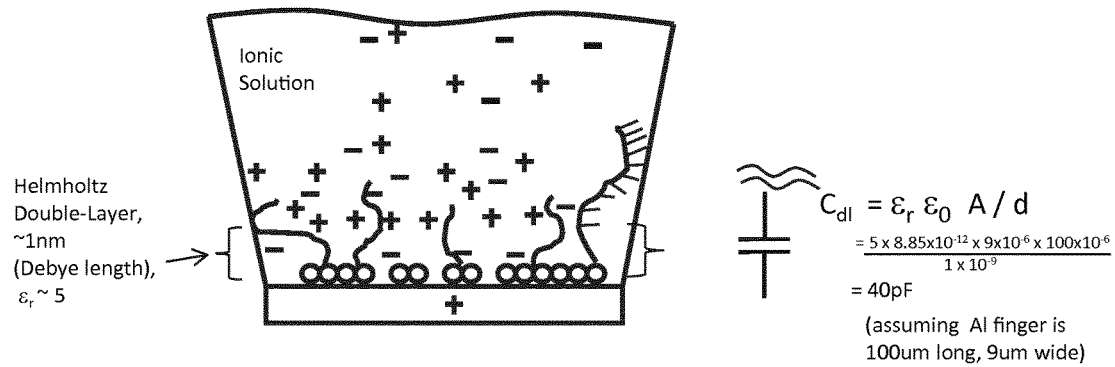
FIG. 5 is a nano-metre scale view of an electrode surface showing SAM and Debye layer.

In similar fashion, the invention can accomplish quantification of many specific components flowing in complex media by a specific surface functionalization of the sensor. For example with nickel-coating to selectively bind his-tagged proteins, or a thiol self-assembled-monolayer (SAM) to bind DNA or PNA probes. FIG. 5 is a zoom-in to an electrode surface at a nanometre scale, showing PNA probes tethered to a SAM on the sensor surface. It shows the Debye double-layer which forms at the electrode-solution interface. A positive charge on the electrode repels anions in the ionic solution, resulting in a depletion region in the solution (similar to the 'depletion region' formed at a semiconductor P-N junction). The double-layer is typically 1 nm wide; a 9 µm×100 µm electrode has a double-layer capacitance $C_{dk}$~40 pF in the example shown. The depletion width (and therefore $C_{dl}$) is modulated by applied voltage. A larger positive voltage on the electrode widens the depletion layer, reducing $C_{dl}$. When the positive voltage attracts a DNA molecule of similar nanometer dimensions, the DNA molecule binds to the complementary PNA probe, effectively widening the depletion layer further, reducing the capacitance further. This makes the DNA molecule (K=5) much more easily detectable, against the background dielectric constant of the water (K=80).

DNA molecules are negatively charged, so they may additionally be attracted to the surface by temporarily stopping the 32 KHz sigma-delta modulator, and placing a positive voltage on both A and B electrodes of the sensor. PNA probes have no charge, and are preferred in this example, making it easier for the target DNA molecules to approach and bind to the PNA probes. Once bound, a negative voltage is then applied to the A and B electrodes. This repels any non-specifically bound DNA molecules, whereas the specifically-bound target DNA molecules stay tethered at the surface, due to the Watson-Crick complementary binding energies. The 32 KHz modulator then resumes switched-capacitor operation of A and B electrodes to measure capacitance.

As well as capturing and quantifying target DNAs, this method/embodiment is also suitable for capturing RNAs, micro-RNAs, and amplicon Nucleic Acids, e.g. from an upstream amplification reaction such as PCR, LGA, or RPA. Salts, unincorporated primers, dNTPs and enzymes can be washed away using DI water, without removing the captured nucleic acid which are bound to the PNA probes. Thus the dry sensor measurement is not affected by non-specifically deposited material. This method provides a simple cost-efficient alternative to expensive laser and optical based nucleic acid detection methods.

FIG. 17 shows an embodiment in which a TSV chip 350 is mounted in a catheter 351 suitable for insertion in a blood vessel or interstitial fluid, e.g. for capture and detection of circulating micro-RNAs. These cell-free nucleic acids circulating in the blood are emerging as important disease detection biomarkers, but are difficult to assess using conventional methods. The sensor surface(s) are exposed, so that when functionalized with complementary PNA probes, the target miRNAs are captured directly over a period of 30 to 60 minutes. The sensor catheter is then withdrawn, washed if necessary to remove proteins and other non-specific materials, then dried to enable a dry capacitance reading. This greatly facilitates rapid patient monitoring and early disease detection.

In another embodiment, the modulator frequency is varied, for example from 10 Hz to 10 MHz. This enables spectral analysis of the molecules at the surface, to assist distinguishing between big and small particles, or between bound and un-bound molecules. When an electric field is applied across a molecule, charges on the molecule tend to separate and align with the electric field. The ability of the charges to separate, and how fast this redistribution happens, depends on the size of the molecule and how strongly they are bound. Charges that are loosely bound can respond to the electric field at higher frequencies, and vice versa. Therefore, by analyzing the signature peaks and dips in the frequency response, the invention is capable of determining useful extra information about the analyte molecules being measured, by spectral and impedance analysis.

Figure 6:
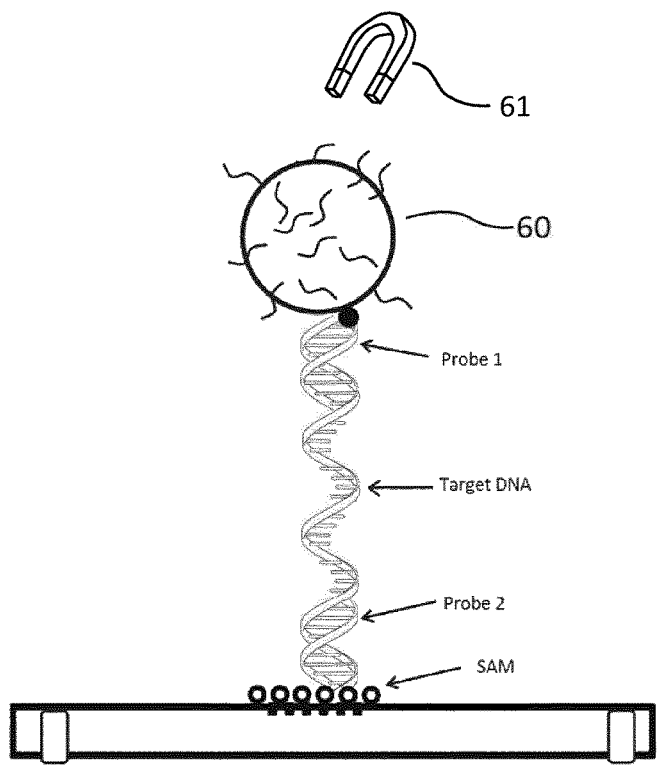
FIG. 6 shows a paramagnetic bead tethered to a self-assembled monolayer (SAM) on the surface of a sensor (bead and probes not to scale, shown bigger for illustration)

Ferrite-Bead-Based Amplification:

Paramagnetic beads are especially useful in molecular biology, e.g. extracting target DNA out of lysate solutions. FIG. 6 shows a 2.8 µm paramagnetic strepdavidin-coated bead 60, flowing or magnetically attracted to the sensor in de-ionised (DI) water from an upstream sample preparation assay. Attached to it is a biotinylated PNA first probe Probe 1, with a target DNA bound to the biotinylated PNA probe in Watson-Crick hybridisation. The DNA becomes bound to a second PNA probe Probe 2 on the sensor 8 surface, i.e. the bead is now tethered to the sensor surface, with the target DNA as ligand. This sandwich-assay structure is highly specific, since the bead can only become tethered if the target DNA is present and bound by two sequence-specific probes. The number of beads becomes a direct proportional indicator of the number of target DNA molecules present in the analyte. K is approximately 10 to 14 for paramagnetic beads, which are a composite of ferrite and polystyrene. This is significantly lower than the K=80 of the background water during 'wet' capacitance measurement (for example in a droplet as shown in the image of FIG. 1(g), and is significantly higher than K=1 of air during 'dry' capacitance measurement (as shown in FIG. 1(h), dry beads on the sensor surface). This, together with their much larger size, makes the beads easier to capacitively measure than the small DNA molecules. Or rephrased, the capacitive sensor can detect much smaller quantities of DNA, as will be further explained in the next pages.

FIG. 7(a) shows a sensor 100 with three interdigitated electrode capacitive sensors Cs2, Cs1, and CRef: a reference, and two sensing structures. FIG. 7(b) shows three analyte droplets on these three sensors:

a positive fluid or buffer solution containing a known amount of beads to be measured;

an analyte channel containing the same fluid or buffer solution, with an unknown amount of beads to be determined; and a negative channel containing the same fluid or buffer solution with none of the target beads present.

FIG. 8(a) shows the negative channel (101), where none of the target beads are present in the fluid. The conductive fluid has a very high dielectric constant, e.g. K=80 for water, and acts as a capacitive 'short circuit', so that the equivalent capacitance between electrodes A and B is $2 \times C_{nitride}$, as shown in FIG. 8(b) equivalent circuit. Assuming relative permittivity (K)=7 for the silicon nitride, a nitride thickness of 2 µm, and electrode finger dimensions of 9 µm×100 µm, we get $C_{nitride}=7 \times \varepsilon_o \times 900/2=28$ fF. For simplicity, the Debye capacitance is ignored in this calculation, since the Debye-layer at the nitride surface (~1 nm depleted insulating layer) is insignificant compared to the 2 µm insulating nitride layer and 2.8 µm beads as shown.

FIG. 8(c) shows the analyte channel (or positive channel) (105) with beads in the fluid introduced or tethered on the nitride surface above the electrodes. This slurry of particles effectively forms a bead layer at the sensor surface and displaces water. This forms a series capacitance $C_{bead}$ in the example shown (2.8 µm beads), see FIG. 8(d) equivalent circuit. The resulting difference in capacitance between the analyte and negative sensors, 5 fF in this example, is measured by the sigma-delta A-to-D converter. By comparing against the capacitance of a known concentration of beads in the positive channel, the capacitance of the analyte channel is now indicative of the number or quantity of beads present in the analyte channel, i.e. the number of target DNA molecules. Ions, proteins, and other molecules which may be present in the fluid are common across all three sensors, therefore are nulled out.

It will be appreciated that as the particles get smaller, e.g nanometre beads or DNA particles, the series capacitance of the particle layer gets bigger, causing the differential capacitance between analyte and negative channels to reduce further, down to attoFarads for example. This can still be detectable by the sigma-delta converter, by extra averaging or by improved filtering of the bit-stream data. Or by evaporating the fluid and performing a 'dry' capacitance measurement of the beads as shown in FIG. 9, this gives a cross-check on the number of beads, for extra accuracy.

FIG. 18 is a real-time plot showing five successive droplets of beads being applied to the sensor over a 50 minute period, with wet and dry capacitance measurements as described above (and similar to the wet and dry salinity assay described above). The vertical axis shows capacitance increasing for each successive addition of beads (0.3 femto-Farads per division). FIG. 19 plots these capacitance increases versus number of beads. In this particular embodiment, a lower limit of 200 beads is detectable. FIG. 1(k) is a SEM photo of approximately 200 beads on the sensor at this limit. Unlike Hall-effect and other magnetic sensors, it does not matter where on the sensor the beads land, they will always be detected due to the capacitive fringe-field at all points of the sensor surface.

Degenerative Bead Signal Amplification:

FIG. 10(a) shows the construction of a standard paramagnetic bead 150. These typically have a ferrite core, and are encased in polystyrene—with strepdavidin coating as in some assays.

FIG. 10(b) shows a bead 155 in which the paramagnetic bead is encased in wax, to improve measurability in liquid. Wax melts at temperatures above 45° C. (e.g. Beeswax or Paraffin Wax). During the measurement in liquid, we heat the sensor chip to ~55° C., using an on-chip or under-chip heater. This temperature begins melting and deforming the wax, as shown in FIG. 10(c). This creates an organic body 156 of integrated beads of low dielectric constant along the sensor surface which excludes liquid. This significantly changes the capacitance at the surface. Even further capacitance change is achieved by including other materials in the wax, e.g. a solute such as salt. This has a low dielectric constant (K~6), and dissolves into the solution after bead deformation. This change of liquid dielectric constant further assists capacitive detection.

The sensor has maximum sensitivity when the particles to be measured are closest to the electrodes. The following are a number of variations of the invention to increase sensitivity:

Reduce the nitride thickness, e.g. from 2 µm to about 1 µm

Increase the electrode thickness, e.g. to 2 µm to about or 3 µm, to create hill/valley topography at the surface. Such topography increases the efficacy of molecules binding to the surface, and increases the capacitance of beads situated 'between' the electrodes, as in FIGS. 8(c) and 9(c) and in the image of FIG. 1(j). Fine-tuning the electrode width and spacing to suit the bead diameter can maximise this sensitivity.

For magnetic beads, place a magnet beneath the sensor IC, to attract the beads to the sensor surface. Magnetic agitation also helps PNA-DNA binding.

The combined effect of these improvements, together with higher oversampling and more filtering in the sigma-delta converter, lowers the limit of detection by an order of magnitude, to about 20 beads or less. And with each bead functionalised on its circumference with at least a few tens of PNA probes, to ensure binding and tethering to the sensor surface with the assistance of magnetic agitation, it now becomes apparent that this simple CMOS capacitive sensor can detect a few hundred DNA molecules directly, i.e. without any PCR, RPA, or any other type of amplification. This means that enzymes, polymerases, dyes and fluorophores can be eliminated from the upstream sample-preparation chemistry, thereby significantly simplifying and shortening the overall assay time, down to an hour or less, and not requiring complicated lasers or optical detection equipment.

Single Base Mismatch and Melting Curve Analysis:

In this assay, a target Nucleic Acid (DNA or RNA) molecule acts as ligand tethering a magnetic bead to a SAM on the surface of the capacitive sensor as shown in FIG. 6. This is due to Watson-Crick pairing of the NA to a first complementary probe on the bead, and to a second complementary probe immobilised on the sensor surface. We employ PNA probes in this assay; they advantageously allow low ionic solutions above the sensor, simplifying capacitance measurements.

A magnet 201 on a head 200 is then introduced over or alongside the beads, as shown in FIG. 11. The beads stay bound initially, due to the NA-PNA Watson-Crick binding energies. The surface is then heated up, by an on-chip or under-chip heater. When temperature reaches the characteristic NA-PNA melting temperature, some bonds breaks and some beads (202) are pulled away under magnetic attraction. This results in a real time capacitance change as shown in FIG. 12(a). In this example a correctly bound 16 bp PNA probe melts at 65° C.

For a known variant with a single base pair difference, the NA may still partially bind to the PNA probe over the remaining 15 bp which match. However the melting temperature for this conformation is 15° C. lower, as shown in FIG. 12(b). The combination of high resolution built-in capacitance sensors, magnetic force producing tension on the tethered paramagnetic beads, and the high specificity of PNA probes results in very good specificity and sensitivity in the melting curve analysis.

These features enable the invention to be used for genotyping. Where the bound target NA is homogenous in sequence, with temperature elevation, the probes will separate (or "melt") from the target NA at the same temperature. However, if the target NA captured is not homogenous, there is the potential for differences in the melting of the probes. A clear example is where there is known variation in DNA at one position where a probe binds, i.e. a single nucleotide polymorphism (SNP), in the population. For an individual being tested, their DNA may contain the most common sequence ("wild type") or the variant ("mutant") only (homozygous) or a combination of both (heterozygous). In a real time analysis of a signal such as capacitance versus temperature, three distinct patterns will be observed. For the homozygous wild type, a change in the plot will be observed at a characteristic temperature, as the wild-type breaks free—FIG. 12(a). For a homozygous mutant, a similar change in plot will be observed but it will occur for a lower temperature—FIG. 12(b). Finally, for a heterozygote, two distinct peaks will be observed, a mix of the patterns for the homozygous plots—FIG. 12(c). Any unknown mutations may also be observed as deviations from the homozygous wild type sequence.

In a variation with multiple sensors and SAM's, we have beads tethered to a first SAM by the wild type sequence above a first sensor, and by the mutant type sequence above a second sensor. A negative control SAM where no beads have attached is above a third sensor. A magnet pulls away beads which are released when the melting temperature is reached. This differential sensing approach enables simultaneous detection, and observation of unknown mutations.

In similar fashion, extension to multiple sensor surfaces with multiple SAM's and multiple probes enables multiplex assays and simultaneous detection of multiple probe-type tethering. For example, FIG. 13(a) shows a sensor IC 251 with four sensor surfaces 252, in a flow channel 250. These are functionalised (or 'spotted') with four different probes, each complementary to, and designed to target four nucleic acid viruses, FIG. 13(b). The four capacitive sensors may be sub-split and interleaved as shown in FIG. 13(c) (260), to average out any 'bunching' or un-equal movement patterns of the beads. Following incubation and binding of any of the target nucleic acids, a magnet then pulls away any unbound NA's as shown in FIG. 11. The resulting bound bead-capacitance measurements of each sensor then indicate which if any of the target NAs are present in the analyte.

It will be appreciated that the invention provides a method of sensing and a sensing apparatus in which there is much improved sensitivity to analytes such as NA and in a low-cost, simple, and robust manner.

FIG. 14 shows a sealed disposable cartridge 300 of the invention, incorporating a TSV IC 303 with radio-frequency transceiver, incorporated in a flow-channel 302 having an inlet 301. The cartridge is made of an injection-moulded thermoplastic polymer, such as Zeonor™ or Topas™. It contains wells where target NA molecules attach to probes on magnetic beads, as part of the NA sample-preparation assay. The 'dry' measurement of the assay is achieved by releasing an air bubble over the sensor surface, or alternatively removing a sealing strip over the sensor surface to allow evaporation. In this embodiment an external magnet 305 is used to control flow of the paramagnetic beads to the TSV Sensor IC embedded at end of channel FIG. 15(a) shows a perspective view of a bench-top apparatus 312 for receiving the cartridge 300 of FIG. 14. It is powered either by a USB or 12V car power outlet, to facilitate portable on-site diagnostic tests. FIG. 15(b) is an expanded cross-section diagram of the apparatus 312. It contains Peltier heaters 314, electromagnets 313, and an inductive power-up and wireless reader circuitry 315. The cartridge 300 is heated and cooled by the heaters 314 for specific melting and binding of NA to probes. The electro magnets move the beads along the flow-channel to the TSV IC 303, for measurement at the sensor surface. The inductive wireless reader powers-up the TSV sensor IC (similar to an RFID chip and reader). The sensor IC then performs the measurements and transmits the results to the bench-top reader 312, for processing and display by the control and display electronics 318

FIG. 16 shows an alternative sensor 320, with 96 TSV sensor ICs of the invention mounted in an 8×12 array identical to standard 96-well SBS footprint. This enables robotic automation of droplet application as shown, facilitating high-volume throughput testing of samples.

It will be appreciated that the invention provides sensors of various embodiments which are compact, portable, robust, and inexpensive to manufacture. They also have sensitivity to presence of nanometre-scale target components. It will also be appreciated that they avoid need for reference electrodes and expensive noble metals. Also, they do not have the corrosion and drift problems associated with electrodes.

The invention is not limited to the embodiments described but may be varied in construction and detail. For example, while most of the embodiments have involved the analyte being part of or attached to particles such as magnetic beads, the analyte may alternatively be dissolved in solution in the sample liquid, thereby changing the dielectric properties. In this case, the drying step would cause precipitation out of the analyte molecules leaving a sediment layer. The processor may take any suitable form, and may indeed be remote from the sensor parts, and in this case may be wirelessly connected.

The invention claimed is:

1. A method of detecting nucleic acid analytes in a liquid sample using a capacitive sensor having inter-digitated electrodes covered by an insulating protective layer, said insulating protective layer providing a sensor surface, the sensor surface comprises a PNA probe fixed on the sensor surface, said probe being selected to bind to the nucleic acid analyte and a processor linked with the electrodes, the method comprising steps of:
bringing the liquid sample into contact with said sensor surface, wherein the liquid sample includes beads attached to nucleic acid analytes, and said beads provide a major part of a capacitance change in which there is an increase in capacitance with increasing number of beads, drying the liquid sample, measuring capacitance of the dried sample by fringe-field sensing in which there is a fixed capacitance portion in the insulating protective layer, and a variable transducer portion in the air or analyte above the insulating protective layer, and using said measurement to provide data concerning the analyte.

2. The method as claimed in claim 1, further comprising: measuring capacitance of the liquid sample before the drying step, and deriving analyte data by comparing measurement of the liquid sample and measurement after drying.

3. The method as claimed in claim 1, wherein said step of bringing the sample into contact with said sensor comprises steps of: attracting nucleic acid analytes to the sensor surface by temporarily stopping the signal processor; placing a positive voltage on a plurality of the electrodes of the sensor; and once the nucleic acid analytes are bound to the PNA probes, applying a negative voltage to said electrodes to repel any non-specifically bound nucleic acid molecules, whereas the specifically-bound target nucleic acid molecules stay tethered at the surface due to the Watson-Crick complementary binding energies.

4. The method as claimed in claim 1, wherein said measuring step comprises using the processor to modulate electrode drive frequency and perform spectral analysis of the nucleic acid analytes at the surface to assist distinguishing between big and small particles, or between bound and un-bound molecules.

5. The method as claimed in claim 1, wherein the beads have a K value higher than K=1; and comprise a composite of ferrite and polystyrene.

6. The method as claimed in claim 1, wherein the beads comprise paramagnetic material encased in a wax material; and the method further comprises at least partially melting the beads on the sensor surface until the beads form a wax layer, and measuring capacitance after said melting.

7. The method as claimed in claim 1, wherein the sensor comprises a multi-layer complementary metal-oxide-semiconductor (CMOS) structure with a heater; and the method further comprises applying a magnetic field to attract the beads to the sensor, and the beads are melted during said drying by operation of said heater.

8. The method as claimed in claim 1, wherein the sensor surface has a plurality of different sensor regions, each with a different probe fixed to the surface, and measuring comprises differential capacitive measurement.

9. The method as claimed in claim 8, a first sensor region binds to a wild type sequence, a second sensor region binds to a mutant type sequence, and a third sensor region is a negative control where no beads bind.

10. The method as claimed in claim 1, wherein the sample is blood and the nucleic acid analyte is micro-ribonucleic acid.

11. The method as claimed in claim 1, wherein, said bringing the liquid sample into contact with said sensor surface is conducted by flow through a flow channel in a device which supports the sensor, the flow channel having wells in which target analyte molecules attach to probes on magnetic beads and the beads are conveyed to the sample by magnetic force.

12. The method as claimed in claim 11, wherein the device comprises an injection-molded thermoplastics polymer forming said flow channels and wells, the device further comprises a wireless transceiver linked to the processor.

13. The method as claimed in claim 11, wherein the device is inserted as a cartridge in a bench-top receiver apparatus for implementation of the method.

14. The method as claimed in claim 11, wherein the sample is heated and cooled by the apparatus for specific melting and binding of NA to probes.

15. The method as claimed in claim 1, wherein the sensor has a CMOS architecture in which CMOS layers provide the sensor electrodes and signal processing circuitry.

16. The method as claimed in claim 1, wherein the sensor surface has a hill and valley topography and at least some of the beads deposit in the valleys so that they have an increased capacitance.

17. The method as claimed in claim 1, wherein the capacitance of the liquid sample is continuously measured during the drying of the liquid sample.

18. The method as claimed in claim 1,
wherein measuring further comprises:
measuring rate of evaporation of the liquid sample while the liquid sample is drying,
measuring capacitance of the dried sample, and
using said capacitance measurement and the rate of evaporation of the liquid sample to provide data concerning the analyte.

\* \* \* \* \*